United States Patent [19]

Oberto et al.

[11] Patent Number: 4,990,446

[45] Date of Patent: Feb. 5, 1991

[54] PROMOTERS FOR THE EXPRESSION OF FOREIGN GENES IN YEAST, PLASMIDS COMPRISING THEM, AND USE THEREOF FOR THE PRODUCTION OF POLYPEPTIDES

[75] Inventors: Jacques Oberto, Steenokkerzeel; John R. N. Davison, Brussels, both of Belgium

[73] Assignee: Labofina, S.A., Brussels, Belgium

[21] Appl. No.: 804,928

[22] Filed: Dec. 5, 1985

[30] Foreign Application Priority Data

Dec. 6, 1984 [BE] Belgium ............................. 0214123

[51] Int. Cl.$^5$ ..................... C12N 15/00; C12N 1/16; C12N 9/24; C07H 15/12; C12P 21/02
[52] U.S. Cl. ............................ 435/69.1; 435/172.3; 435/320.1; 435/255; 435/200; 935/41; 935/37; 935/48; 536/27
[58] Field of Search ............... 435/68, 70, 172.3, 320, 435/255, 200, 201, 206; 935/14, 28, 37, 60, 69; 536/27

[56] References Cited

PUBLICATIONS

Dobson et al., Conservation of High Efficacy Promotor Sequences in *Saccharomyces Cerevisiae* NAR (1982), 10:8, 2625–2637.

Hitzman et al, Secretion of Human Interferons by Yeast Science (1983), 219, 620–624.

Guarantc et al., Improved Methods for Maximizing Expression of a Coned Gene: a Bacterium that Synthesis Rabbit B Globin Cell 1980 20:543–553.

Rothstein et al., Secretion of a Wheat & Amylase Expressed in Yeast, Nature (1984), 308:12, 662–665.

*Primary Examiner*—Thomas G. Wiseman
*Assistant Examiner*—Patricia Carson
*Attorney, Agent, or Firm*—Roger W. Parkhurst; John K. Abokhair; M. Norwood Cheairs

[57] ABSTRACT

Promoters capable of ensuring expression in yeast of genes coding for heterologous polypeptides are disclosed, which comprise a DNA fragment or mutants or sub-fragments thereof, said promoter comprising a definite nucleotide sequence commencing with an EcoRI site and terminated by another restriction site. Also disclosed are vector plasmids containing the promoters, transformed yeasts comprising these plasmids, and a process for preparing polypeptides and especially a 1,4-β-N-acetylmuramidase.

20 Claims, 12 Drawing Sheets

```
     EcoRI                      RsaI                        MboI
       |                          |                           |
GAATTCACTGGATTCCTTCCTACCGGTACCAATATCACTGTAAATATGTCTTCAGATCCTTGAACTGGAAGTATTTAGCG
             20                         40                         60                         80

TCCCTGACTTTCATCAACTGAAAGTCAAGCTCATTTGTAAATTGTCCCCTCTTTTTATACAAATTTTCTGGCAGAATTGA
             100                        120                        140                        160

CAGGAAATCCTCCTTAACTAAATATGGATTGTAGCTTCTATATTGTAAGACAGAAGGTTTCTTTTCCTGCAACTGCTGCT
             180                        200                        220                        240

GCTTATTAACAGATGCCGTTTTCTCACTTATTGTTGCTGAATTTCCTGACTCTACGGAGCCAAGAACTCTTCCCGTGGAC
             260                        280                        300                        320
       RsaI                                                  ClaI
         |                                                    |
TTCAGATGGTTCAGTACTAATTTAATAGCTTTACTAGAAGCCTTCATATCTGCTTTACATCGATGACAAAGGGATAATGG
             340                        360                        380                        400

GTAGAGTCTGGCACTCCTACCCTAAATTGTTAACTTCCTATTTGAGTTCGTGGTGTTAGTATTCTCATCACGATTAACGA
             420                        440                        460                        480

ATATGAAAAAAAAAATTGAAAATTTTGTAGAAACGGAGTGCTCAG[TATAAAA A]GCGCATAGTAAGACTTTTTGTTAA[ATG]
             500                        520                        540                        560
                                                                                    MboI
                                                                                      |
TTTCTTTCCTCCTATACATTTTCACATA[CTTTTCTTTCTTTTTTGTTT T]AAAACCTG[CAAG C]AGCTTTACA GATCCGGAGC
             580                        600                        620                        640

TTGGCTGTTGCCCGTCTCACTGGTGAAAAGAAAAACCACCCTGGCGCCCAATACGCAAACCGCCTCTCCCCGCGCGTTGG
             660                        680                        700                        720
       PvuII
         |
CCGATTCATTA[ATG]CAGCTGGCACGACAGGTTTCCCGACTTAATCGCCT
             740                        760                        780                        800
                                     FIG.3
```

PROMOTERS FOR THE EXPRESSION OF FOREIGN GENES IN YEAST, PLASMIDS COMPRISING THEM, AND USE THEREOF FOR THE PRODUCTION OF POLYPEPTIDES

TECHNICAL FIELD

The present invention relates to fragments of yeast DNA comprising a promoter capable of ensuring the expression in yeast of genes coding for polypeptides, generally for heterologous polypeptides. It also relates to vector plasmids comprising said fragments and to yeasts transformed by said plasmids.

BACKGROUND OF THE INVENTION

New genetic engineering techniques permit the expression in various organisms of genes coding for foreign proteins. One example of this, among many others, is the synthesis of human interferons by the yeast *Saccharomyces cerevisiae* (R. A. Hitzman et al., Science 219, 1983, 620).

A prerequisite of the expression of a gene in yeast is the location, upstream thereof, of a yeast promoter which is recognized by the yeast RNA polymerase II and causes the synthesis of the corresponding RNA messenger. Several such yeast promoters have already been described. In many cases, however, the expression levels obtained were low and impractical for industrial applications, especially when the promoters were used for the expression of foreign genes (T. Atkinson et al., Biochemical Soc. Trans. 12, 1984, 215).

There is a need for efficient promoters for genetic manipulation of yeasts in such a way that they can be used for practical purposes.

SUMMARY OF THE INVENTION

An object of the present invention is to provide such promoters. Another object is to provide vector plasmids, wherein said promoters are fused with heterologous genes so as to ensure the expression in yeast of said heterologous genes in the corresponding polypeptides. The yeasts transformed by said plasmids are a further object of the invention, as are the new polypeptides produced by said yeasts. Still another object is to provide a process for producing polypeptides by growing said transformed yeasts.

These various objects are accomplished by using as a base promoter a fragment of yeast DNA, or mutants or sub-fragments thereof which have retained the promoter function, having a nucleotide sequence beginning with an EcoRI site and selected from the following sequences, and having another restriction site which immediately follows said sequence: SEQUENCE ONE, which is herein defined to be:

```
         10         20         30         40         50         60         70
GAATTCACTGGATTCCTTCCTTCCGGTACCAATATCACTGTAAATATGTCTTCAGATCCTTGAACTGGAA 80         90        100        110        120        130        140
GTATTTAGGGTCCCTGACTTTCATCAACTGAAAGTCAAGCTCATTTGTAAATTGTCCCCTCTTTTTATAC 150        160        170        180        190        200        210
AAATTTTCTGGCAGAATTGACAGGAAATCCTCCTTAACTAAATATGGATTGTAGCTTCTATATTGTAAGA 220        230        240        250        260        270        280
CAGAAGGTTTCTTTTCCTGCAACTGCTGCTGCTTATTAACAGATGCCGTTTTCTCACTTATTGTTGCTGA 290        300        310        320        330        340        350
ATTTCCTGACTCTACGGAGCCAAGAACTCTTCCCGTGGACTTCAGATGGTTCAGTACTAATTTAATAGCT 360        370        380        390        400        410        420
TTACTAGAAGCCTTCATATCTGCTTTACATCGATGACAAAGGGATAATGGGTAGAGTCTGGCACTCCTAC 430        440        450        460        470        480        490
CCTAAATTGTTAACTTCCTATTTGAGTTCGTGGTGTTAGTATTCTCATCACGATTAACGAATATGAAAAA 500        510        520        530        540        550        560
AAAAATTGAAAATTTTGTAGAAACGGAGTGCTCAGTATAAAAAGCGCATAGTAAGACTTTTTGTTAAATG 570        580        590        600        610        620        630
TTTCTTTCCTCCTATACATTTTCACATACTTTTCTTTCTTTTTGTTTTAAAACCTGCAAGCAGCTTTACA 640        650        660        670        680        690        700
GATCCGGAGCTTGGCTGTTGCCCGTCTCACTGGTGAAAAGAAAAACCACCCTGGCGCCCAATACGCAAAC 710        720        730
CGCCTCTCCCCGCGCGTTGGCCGATTCATTAATG;
```

SEQUENCE TWO, which is herein defined to be:

```
         10         20         30         40         50         60         70
GAATTCACTGGATTCCTTCCTACCGGTACCAATATCACTGTAAATATGTCTTCAGATCCTTGAACTGGAA 80         90        100        110        120        130        140
GTATTTAGGGTCCCTGACTTTCATCAACTGAAAGTCAAGCTCATTTGTAAATTGTCCCCTCTTTTTATAC 150        160        170        180        190        200        210
AAATTTTCTGGCAGAATTGACAGGAAATCCTCCTTAACTAAATATGGATTGTAGCTTCTATATTGTAAGA 220        230        240        250        260        270        280
CAGAAGGTTTCTTTTCCTGCAACTGCTGCTGCTTATTAACAGATGCCGTTTTCTCACTTATTGTTGCTGA
```

-continued

```
        290        300        310        320        330        340        350
ATTTCCTGACTCTACGGAGCCAAGAACTCTTCCCGTGGACTTCAGATGGTTCAGTACTAATTTAATAGCT 360        370        380        390        400        410        420
TTACTAGAAGCCTTCATATCTGCTTTACATCGATGACAAAGGGATAATGGGTAGAGTCTGGCACTCCTAC 430        440        450        460        470        480        490
CCTAAATTGTTAACTTCCTATTTGAGTTCGTGGTGTTAGTATTCTCATCACGATTAACGAATATGAAAAA 500        510        520        530        540        550        560
AAAAATTGAAAATTTTGTAGAAACGGAGTGCTCAGTATAAAAAGCGCATAGTAAGACTTTTTGTTAAATG 570        580        590        600        610        620        630
TTTCTTTCCTCCTATACATTTTCACATACTTTTCTTTCTTTTTGTTTTAAAACCTGCAAGCAGCTTTACA 640        650        660        670        680        690        700
GATCCGGAGCTTGGCTGTTGCCCGTCTCACTGGTGAAAAGAAAAACCACCCTGGCGCCCAATACGCAAAC 710        720        730        740
CGCCTCTCCCCGCGCGTTGGCCGATTCATTAATGCAGGG;
``` and SEQUENCE THREE, which is herein defined to be:

```
         10         20         30         40         50         60         70
GAATTCACTGGATTCCTTCCTACCGGTACCAATATCACTGTAAATATGTCTTCAGATCCTTGAACTGGAA 80         90        100        110        120        130        140
GTATTTAGGGTCCCTGACTTTCATCAACTGAAAGTCAAGCTCATTTGTAAATTGTCCCCTCTTTTTATAC 150        160        170        180        190        200        210
AAATTTTCTGGCAGAATTGACAGGAAATCCTCCTTAACTAAATATGGATTGTAGCTTCTATATTGTAAGA 220        230        240        250        260        270        280
CAGAAGGTTTCTTTTCCTGCAACTGCTGCTGCTTATTAACAGATGCCGTTTTCTCACTTATTGTTGCTGA 290        300        310        320        330        340        350
ATTTCCTGACTCTACGGAGCCAAGAACTCTTCCCGTGGACTTCAGATGGTTCAGTACTAATTTAATAGCT 360        370        380        390        400        410        420
TTACTAGAAGCCTTCATATCTGCTTTACATCGATGACAAAGGGATAATGGGTAGAGTCTGGCACTCCTAC 430        440        450        460        470        480        490
CCTAAATTGTTAACTTCCTATTTGAGTTCGTGGTGTTAGTATTCTCATCACGATTAACGAATATGAAAAA 500        510        520        530        540        550        560
AAAAATTGAAAATTTTGTAGAAACGGAGTGCTCAGTATAAAAAGCGCATAGTAAGACTTTTTGTTAAATG 570        580        590        600        610        620
TTTCTTTCCTCCTATACATTTTCACATACTTTTCTTTCTTTTTGTTTTAAAACCTGCAAGGG.
```

Specific promoters of the present invention include: SEQUENCE ONE immediately followed by a PvuII site (CAGCTG sequence at 735-740); and SEQUENCE TWO or SEQUENCE THREE immediately followed by BamHI site (GGATCC sequence at 740-745 or 623-628, respectively). The basic sequence may be followed by other restriction sites in other promoters.

BRIEF DESCRIPTION OF THE FIGURES

In the detailed description of the invention given hereafter and in the examples, reference will be made to the appended drawings in which:

FIG. 3 shows the sequence of promoter p415 comprising the yeast sequence located between sites EcoRI and MboI, and wherein appear several elements currently found in other strong yeast promoters: the TATA box, the CT block, closely followed by the CAAGC sequence.

FIG. 13 illustrates SEQUENCE II.

FIG. 14 illustrates SEQUENCE III.

DETAILED DESCRIPTION OF THE INVENTION

Method employed to isolate the base promoter

Isolation of the base promoter of the invention, hereinafter called p415, involves known methods. It relies on the observation (L. Guarente, Meth. Enzymol. 101, 1983, 181; M. J. Casadaban et al., ibid. 100, 183, 293) that the gene lacZ coding for the β-galactosidase of E. coli can, under certain conditions, be expressed in the yeast S. cerevisiae and that this expression can be monitored by the blue color of the yeast colonies when grown on the chromogenic indicator X-gal. This blue color is due to hydrolytic cleavage of the indicator by β-galactosidase, and the rate of this cleavage depends on the amount of β-galactosidase synthesized.

Therefore, the blue color of the colony depends on the efficiency of β-galactosidase expression, which in turn depends, among other things, on the force of the yeast promoter used. Thus, among a selection of yeast promoters, the strongest may give the blue color more rapidly, and this can be verified quantitatively by enzyme assay of β-galactosidase activity.

Construction of a probe for isolating yeast promoters

A prerequisite for the isolation of yeast promoters according the above method, is a vector capable of replication and selection in yeast, that contains the lacZ gene of E. coli but does not express this in yeast due to the absence of a suitable promoter. This vector further has to fulfill the following conditions. It should be capable of replicating in the yeast by means of a sequence recognized by the replication machinery of the yeast. It should be capable of selection and maintenance in yeast due to the presence of a marker gene. It should be potentially capable of expressing the lacZ gene in yeast when given a suitable promoter. It should comprise a unique restriction site upstream of this gene, for the insertion of small fragments of yeast DNA likely to comprise a promoter.

Figure 1:
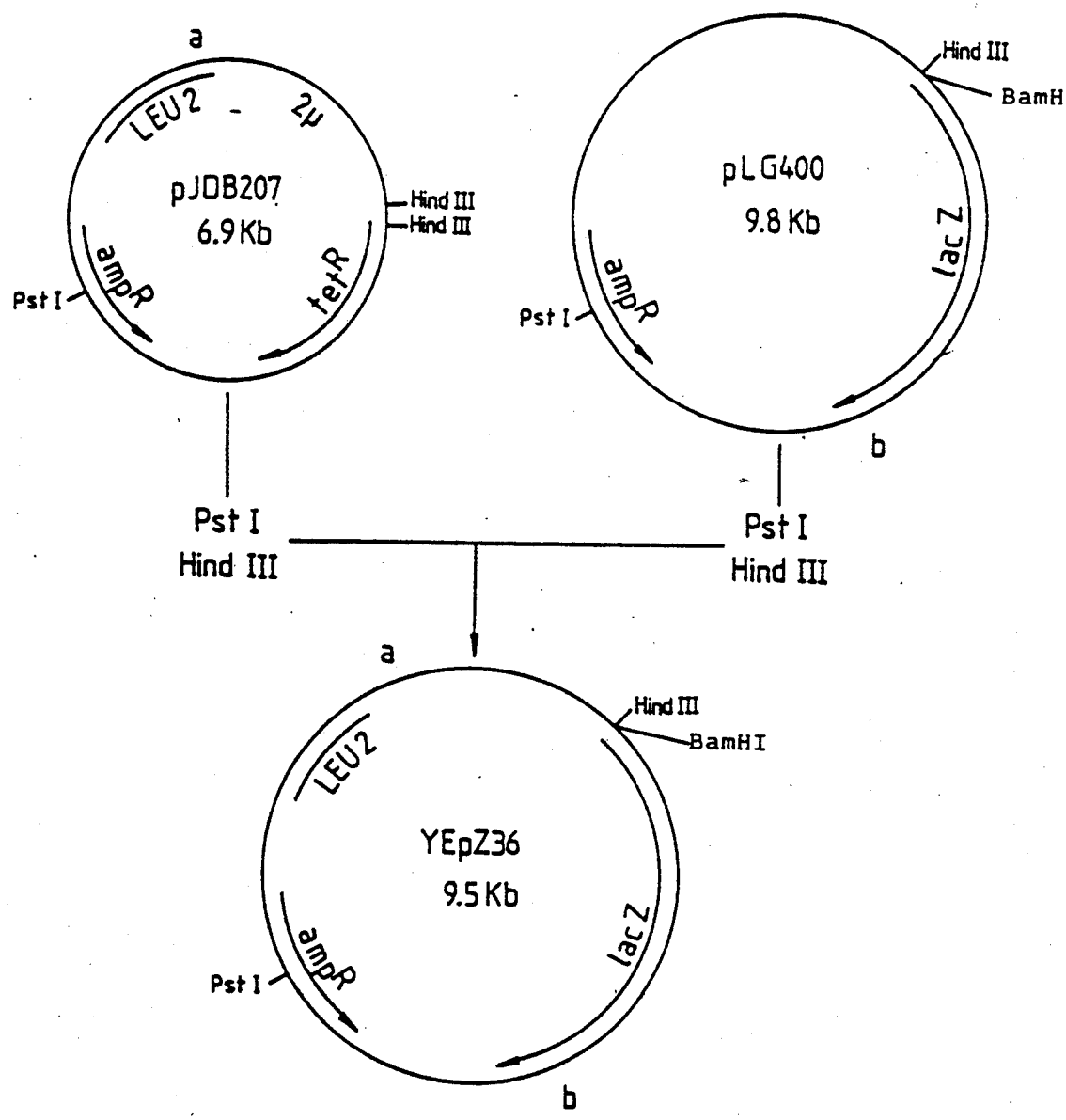
FIG. 1 represents the construction of plasmid YEpZ36 used as a probe for isolating yeast promoters. This construction is obtained by ligation of a fragment from plasmid pJDB207 containing the LEU2 marker gene and the 2-micron yeast plasmid replication origin with a fragment from plasmid pLG400 containing the lacZ gene coding for the Escherichia coli β-galactosidase.

The construction of such a vector is outlined in FIG. 1. Two known plasmids, pJDB207 (J. D. Beggs et al., Nature 283, 1980, 836) and pLG400 (L. Guarente et al., Cell 20, 1980, 543), were combined using classical techniques. This combination resulted in plasmid YEpZ36 that is capable of replication in S. cerevisiae by virture of the replication origin of the 2-micron endogenous plasmid from pJDB207. It also carries the LEU2 marker gene which makes it capable of selection and maintenance in yeast having a leu2− mutation. It has a unique BamHI site where small fragments generated by the MboI restriction enzyme can be inserted.

Construction of plasmid YEpZ415 comprising promoter p415

Isolation of the promoter of the present invention with the above-described promoter probe vector was carried out as follows.

DNA fragments resulting from a partial digest, with the MboI restriction enzyme of total DNA of S. cerevisiae KL14-4A (G. Fage et al., J. Mol. Biol. 99, 1975, 203), were inserted into the BamHI site of the above-described plasmid YEpZ36, and the recombinant DNA thus obtained was used to transform the leu2− strain of S. cerevisiae GRF18. The transformed yeast colonies were screened on X-gal medium for β-galactosidase production. Several clones appeared positive upon transfer to X-gal medium, and the most active one, as determined by β-galactosidase assays, was selected for the isolation of the promoter of the invention.

Figure 2:
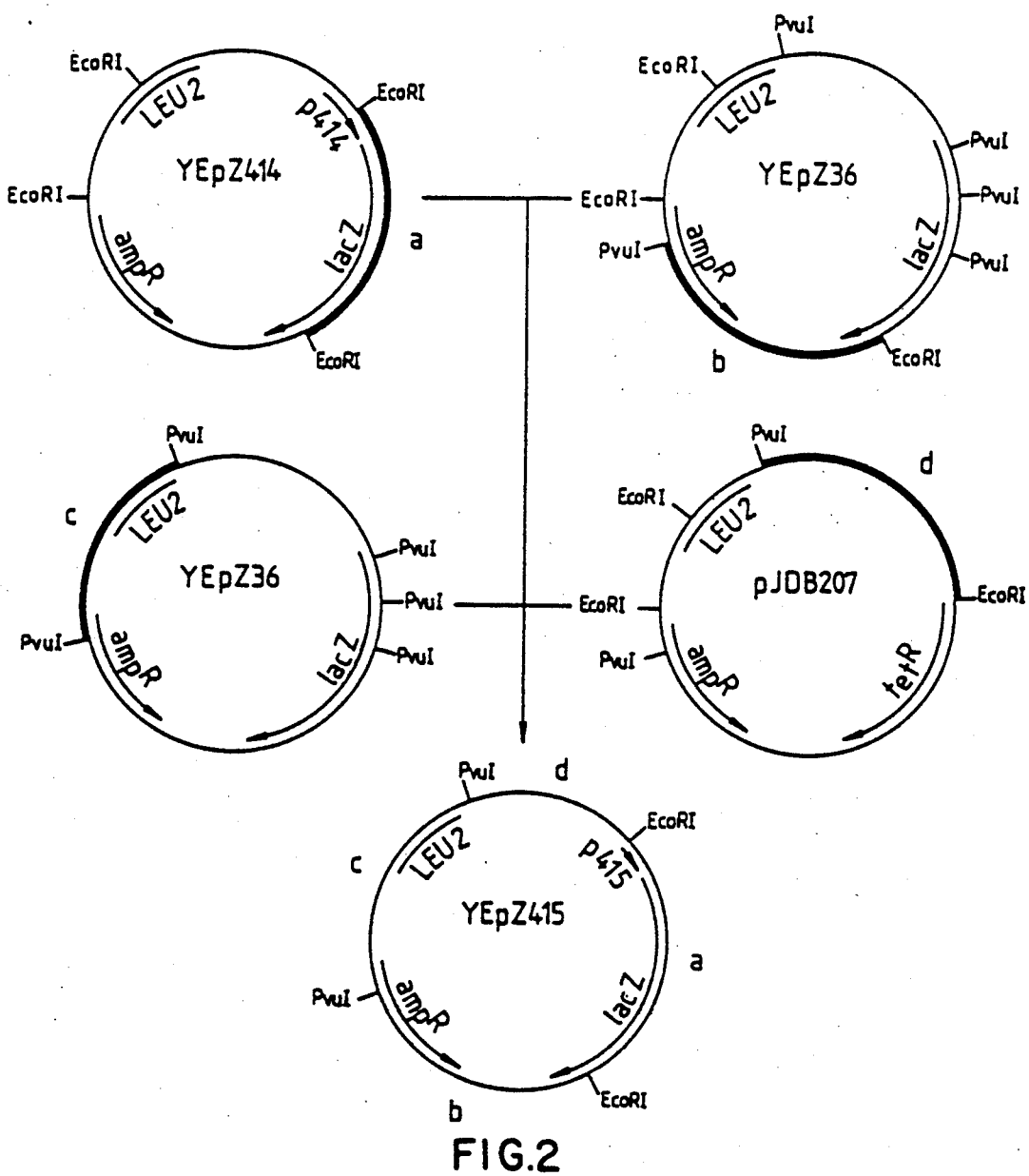
FIG. 2 represents the construction of plasmid YEpZ415 bearing the base promoter of the invention (p415) by ligation of four fragments from plasmids YEpZ36, YEpZ414 and pJDB 207.

Plasmid DNA from this clone isolated after transfer to E. coli, showed a 980 bp insert, that contained an EcoRI site 630 bp before the β-galactosidase gene. The promoter ensuring transcription of the β-galactosidase gene was found to be associated to this 630 bp fragment, as replacement of the 350 bp fragment preceding the EcoRI site did not affect β-galactosidase activity. The method of construction, whereby the 350 bp fragment was deleted, is detailed in FIG. 2, where the initial 980 bp fragment is referred to as p414. The DNA sequence of the 630 bp fragment with the beginning of the lacZ gene of E. coli was determined according to the method of A. M. Maxam and W. Gilbert (Proc. Acad. Sci. U.S.A. 74, 1977, 560; Methods Enzymol. 65, 1980, 499) and is shown in FIG. 3. Two translation initiation codons (ATG) are present in the correct reading frame at positions 558 and 732. However, the results of a subcloning experiment have shown that only the lacZ proximal ATG (position 732) is active. It is interesting to note tha this ATG is not the initiator codon of a yeast gene, but part of the E. coli lacI gene that was used in the construction of the pLG400 vector (Guarante et al., Cell, 20, 1980, 543). For clarity, the fragment comprised between sites EcoRI and PvuII, and comprising the latter ATG, will hereinafter be referred to as the p415 promoter.

Arrangement of promoter p415 to make it easily usable

To improve the ease of handling of the p415 promoter isolated as described above, both ends were flanked with unique restriction sites in current use. In this way, it can be moved from one plasmid to another, according to the application envisioned, and downstream insertion of a foreign gene for expression from the promoter is facilitated.

The following examples describe the details of a construction giving plasmid YEpZ101, wherein the promoter of the invention is associated upstream to a HindIII fragment and downstream to a BamHI fragment, this latter being able to serve for the introduction of foreign genes, as also described in the examples. However, other constructions whereby the p415 promoter would be flanked with other restriction sites as EcoRI, ClaI, HindIII, SphI, SalI, SacI, PstI, XbaI, XhoI can evidently also be considered, and the variants thus obtained of this promoter are within the scope of the invention.

Deletion variants of promoter p415

Figure 4:
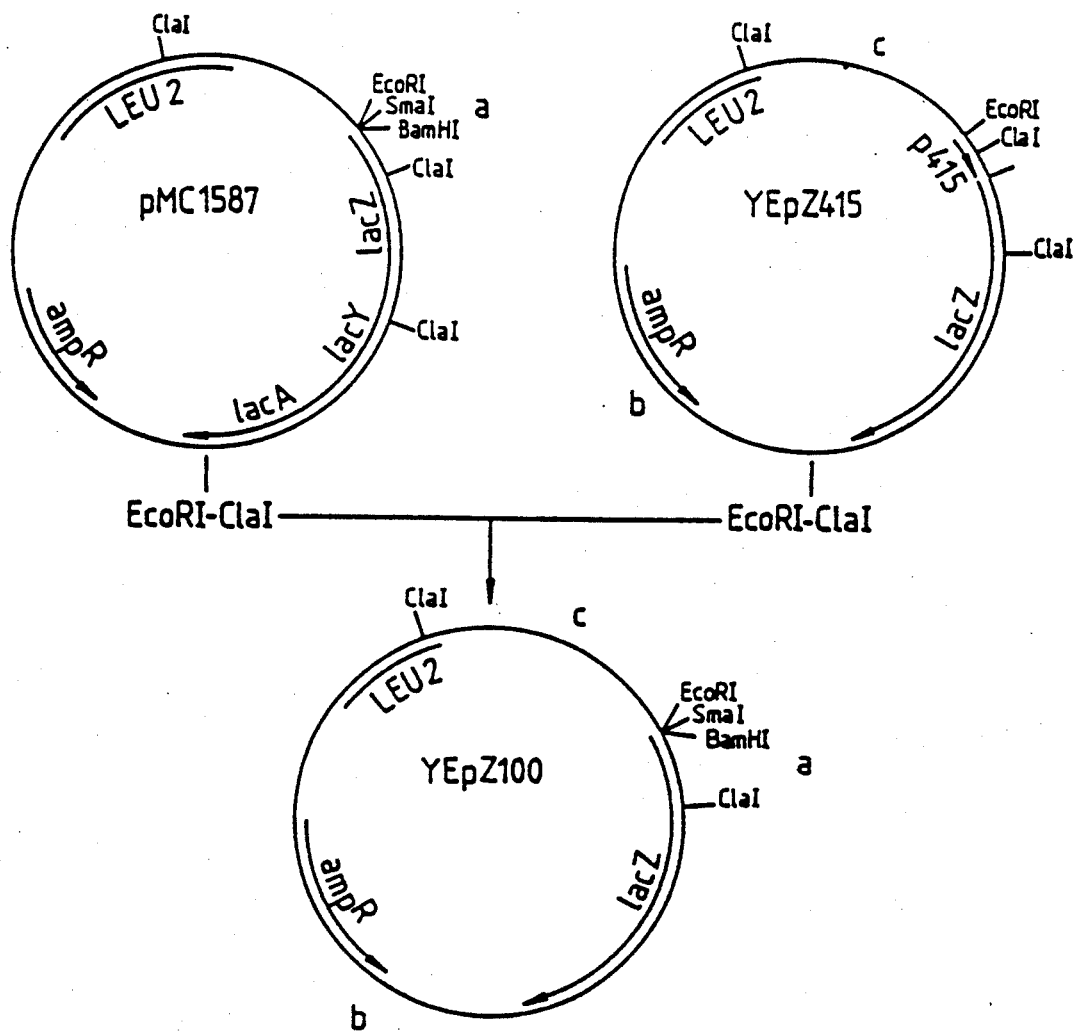
FIGS. 4 and 5, respectively, represent the construction of plasmids YEpZ100 and pJ04 which in their turn are used, as shown by FIG. 6, for the construction of plasmid YEpZ101 comprising a variant of promoter p415 associated to a HindIII-BamHI fragment.

Other varients of promoter p415, obtained by various deletions, also bring practical advantages. As a matter of fact, promoter p415 as it is included into lasmid YEpZ101 is advantageous for the expression of a gene, such as the lacZ gene of pMC1587 or YEpZ100 (FIG. 4), that lacks an ATG initiator codon, since this is provided by the promoter itself just upstream of the BamHI site. However, in the case of a gene that already has its own initiator codon, promoter p415 of plasmid YEpZ101 cannot be used as such. It is indeed known that in eucaryotes, yeast included, the first ATG codon of the messenger RNA is normally used. Thus a second ATG introduced would have one of two effects, according to whether it would be in phase or out of phase with the ATG codon of the promoter. In the latter case, a polypeptide would be produced which would be totally different from that coded by the gene. In the former case, the amino acids corresponding to the codons between the first and the second ATG's would be added to the polypeptide at the amino end. Thus, a polypeptide differing from that normally coded by the gene, though perhaps not inactive, would be obtained; this is unfavorable since substitutes as close as possible to the natural products are sought in most genetic engineering applications. This situation is especially unfavorable when it is also attempted to make use, as in the examples, of the signal sequence of a natural product to ensure its export outside of the transformed yeast cell.

For the above considerations, it was necessary to have variants of promoter p415 not comprising the ATG initiator codon, while retaining the immediately downstream restriction site. The following examples describe such deletions from plasmid YEpZ101, starting from site BamHI. Several variants of promoter p415 were obtained which comprise a BamHI site at various distances from the HindIII end: p415Δ 2, p415Δ 4 and p415Δ 5. It is obvious that the BamHI and HindIII ends in these variants can be replaced by other restriction sites just as in the case of the original p415 promoter.

One of the variants, p415Δ 4, proved particularly good for the expression of the chicken lysozyme gene in yeasts. This result, in itself is surprising considering the present knowledge of translation and transcription in yeast, demonstrates that other modifications of promoter p415, obtained either by the same technique or by any other in vitro or in vivo method, could effect improvements with respect to the results described in the present application. The different variants thus obtained are evidently also to be considered as being within the scope of the present invention.

Yeast transformations by vector plasmids comprising promoter p415 or variants thereof As one skilled in the art realizes, the promoters according to the invention can be used to express foreign genes in yeast if they are correctly associated to the gene to be expressed in a vector plasmid capable of replication into an as high as possible number of copies. This vector should therefore comprise a replication origin recognized by the host cell, and also a marker gene allowing visualization and selection of the cells which have effectively been transformed by the plasmid.

A great number of expression vectors comprising these different elements have been constructed, especially for the transformation of yeasts of the *S. cerevisiae* species. They generally comprise either the replication origin of the 2-micron plasmid present in most strains of this species, or even an autonomous ARS replication segment of chromosomal origin.

A gene coding for an enzyme involved in the biosynthesis of an essential metabolite, e.g., an amino acid, is generally used as a marker. The host cell is then used in a yeast strain which has become by mutation auxotrophic for said metabolite. When growing this strain on a medium free of said metabolite, only those cells transformed by a plasmid carrying the missing gene will be able to grow. Typical examples of such markers are the LEU2 and TRP1 genes coding for an enzyme involved in the biosynthesis of leucine and tryptophane, respectively. These expression vectors should also comprise one or preferably several restriction sites for inserting the coding part of interest and the various elements required for optimizing the expression thereof, e.g., promoters, terminators and other control elements.

In addition, these plasmids often comprise bacterial sequences capable of ensuring their replication and selection in an intermediate bacterial host, e.g., *E. coli*. Classical examples of such shuttle plasmids are cited YEp13 (J. R. Broach et al., Gene 8, 1979, I21), pFL1-4 (M. R. Chevallier et al., Gene 11, 1980, 11), and pJDB207 (J. D. Beggs, Alfred Benson Symposium No. 16, Munksgaard, Copenhagen 1981, p. 383).

According to a preferred embodiment of the invention, mainly when the host cell belongs to the *S. cerevisiae* species, the plasmid used comprises at least the REP functions of the 2-micron endogenous plasmid sequence. These functions generally give a better stability to the plasmid, especially if the host cell has previously been cured of its 2-micron plasmids (C. P. Holenberg, Curr. Top. Microbiol. Immunol. 96, 1982, 119; R. M. Walmsley et al., Mol. Gen. Genet., 1983, 261). Classical examples of such vectors are plasmids pJDB219 and pJDB248 (J. D. Beggs, Nature 275, 1978, 104). Another vector of this type is described in the following examples.

These various plasmids may be used as vectors to ensure expression in yeast of heterologous genes suitably positioned upstream of the promoters of the invention. Examples of particular constructions are given as illustrations in the present application, but many other possibilities exist, and various combinations of replication origins, marker genes and other structural elements may be used to obtain similar results. The various expression vectors which can thus be constructed to express heterologous genes by virtue of the promoters of the invention must be considered as being within the scope of the invention.

The transformed cells obtained in these various cases are also part of the invention. Although most of the techniques developed to transform yeast cells have been applied to the *S. cerevisiae* species, the invention also comprises the cells obtained by transforming other species and genera of yeast with expression vectors of the type described above. Examples of other yeasts include *Saccharomycopsis lipolytica, Schizosaccharomyces pombe, Kluyveromyces lactis*, etc. However, according to a preferred embodiment of the invention, transformable host cells from the *Saccharomyces* genes and preferably from the *S. cerevisiae* species will be used. Examples of transformable strains from this species include AH22 and GRF18 amongst many others.

Polypeptide production by transformed yeasts

The DNA fragments which can be expressed in yeast according to this invention may have various origins. They may be procaryotic genes, as the E. coli β-galactosidase gene whose expression is described in one of the following examples. The DNA fragment may also be an eucaryotic gene so long as it does not comprise introns as yeast is unable to ensure maturation of the messenger RNA from the transcription of fragmented genes (J. D. Beggs et al., Nature 283, 1980, 835). In this case, however, it is possible to express the corresponding cDNA, as described below in another example showing chicken lysozyme expressed in yeast. Many other genes can similarly be expressed, whether they are of bacterial, vegetable, animal or human origin. New polypeptides that would thus be expressed are also within the scope of the invention.

When a yeast strain has been induced according to the present invention to produce one or another of these polypeptides, it is necessary to multiply it under the conditions most favorable to its growth in order to take advantage of this new property. One skilled in the art will easily determine these conditions according to the characteristics peculiar to the yeast strain used as host. As transformed yeasts have in most cases, a more or less important tendency to lose artificially-constructed plasmids, it is advantageous to use a culture medium so as to exert a positive selection pressure on them. When the strain is an auxotrophic mutant for one or another essential metabolite and when the vector plasmid used comprises a marker gene capable of restoring the strain prototrophy, e.g., the LEU2 or TRP1 genes mentioned above, this selection pressure may be exerted by omitting said metabolite from the culture medium. If, on the contrary, the plasmid comprises as marker a gene capable of conferring to the yeast a more or less marked resistance to a growth inhibitor, e.g., an antibiotic such as G418 (J. Jimenez and J. Davies, Nature 287, 1980, 869) or an herbicide such as diuron (Belgian Patent No. 899,607 of the Applicant), the selection pressure in favor of the transformed yeast can be applied by growing it in a medium supplemented with this inhibitor. Other means exist to obtain the same result and may also be used to practice the invention.

When transformed yeasts have been grown under conditions ensuring the best production of the polypeptide of interest, this polypeptide still has to be recovered. Many techniques are available which those skilled in the art will combine to obtain in each case the best recovery yield and the greatest purity of the desired polypeptide. However, according to a preferred embodiment, the gene expressed upon intervention of promoter p415 or one of the variants thereof will preferably be equipped with a leader sequence coding for a signal peptide capable of ensuring the transport of the product through the plasmid membrane of the transformed cell. In this case, the separation of the polypeptide formed will indeed be considerably easier, whether it is liberated into the medium from where it will be recovered by classical methods, including adsorption and/or precipitation, or it remains associated with the yeast wall from where it will have to be separated by other methods.

The various aspects of the invention will appear more specifically in the following examples which are purely illustrative and should not be construed to limit the scope of the invention.

EXAMPLES

1. Expression of E. coli β-galactosidase in S. cerevisiae by YEpZ415

Plasmid YEpZ415, the construction of which contributed, as hereabove described, to the isolation of promoter p415 according to the invention, was used to transform S. cerevisiae GRF18 (Leu−, His−) yeast strain with selection of the clones prototrophic for leucine.

The specific β-galactosidase activity of these clones was measured on cellular extracts by the method of M. J. Miller (Experiments in Molecular Genetics, 1972, Cold Spring Harbor Laboratory, Cold Spring Harbor, N.Y.), as modified by M. Crabeel et al. (EMBO J., 2, 1983, 205). The protein concentration of the extracts has on the other hand been determined by the method of M. M. Bradford (Anal. Biochem. 72, 1976, 1948). The specific activity was of 7733 β-galactosidase units, corresponding to 2.57% of the total proteins of the extract.

2. Expression of the E. coli β-galactosidase gene in S. cerevisiae by plasmid YEpZ101

In this example, promoter p415 according to the invention was flanked by two restriction sites commonly used in genetic engineering (HindIII and BamHI), and used in this form to express the lacZ gene of E. coli in a plasmid called YEpZ101. This operation was carried out in several steps which required the construction of two intermediate plasmids: YEpZ100 and pJ04.

2.1 YEpZ100 (FIG. 4) was constructed from pMC1587 (M. J. Casadaban et al., Methods in Enzymology 100, 1983, 293) and YEpZ415 of which it combines the advantages: it has the beginning of the lacZ gene and the group of restriction sites EcoRI, SmaI and BamHI of pMC1587; it has the end of the lacZ gene of YEpZ415, whereby the lacY and lacA genes of pMC1587 are eliminated, which would uselessly increase the size of the plasmid; it has the further advantage of maintaining the high number of copies characteristic to the plasmids derived from pJDB207, e.g., YEpZ415 (E. Erhart and C. P. Hollenberg, J. Bacteriol. 156, 1983, 625).

Figure 5:
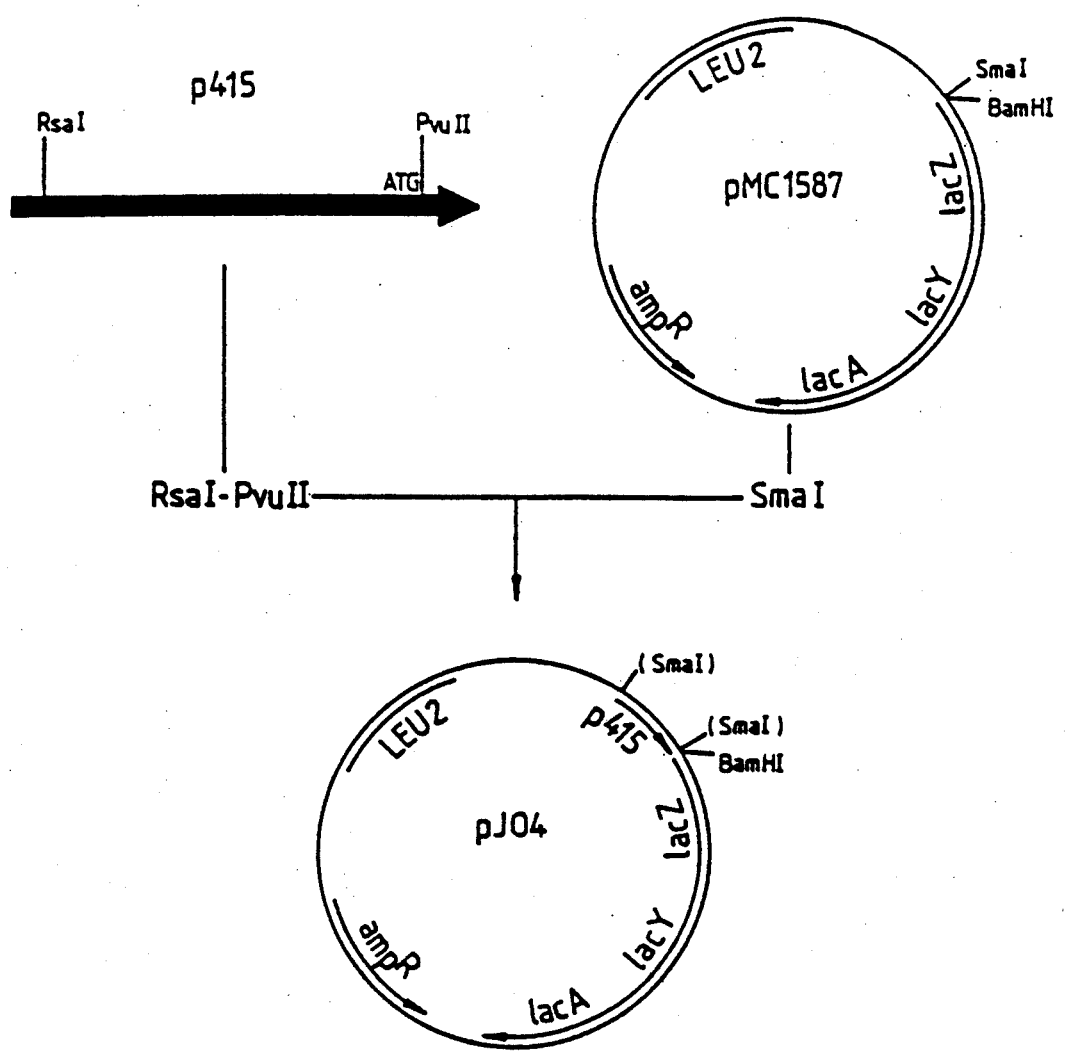

2.2 pJ04 (FIG. 5) was constructed by introducing the RsaI-PvuII fragment of promoter p415 (FIG. 3) into the SmaI site of plasmid pMC1587. The operation has three results:

(i) the ATG initiation codon immediately upstream of site PvuII is retained;
(ii) the PvuII site of p415 and the SmaI site of pMC1587 are destroyed;
(iii) a BamHI site is introduced immediately downstream of the ATG initiator codon. This site is often used for the cloning of foreign genes.

Figure 6:
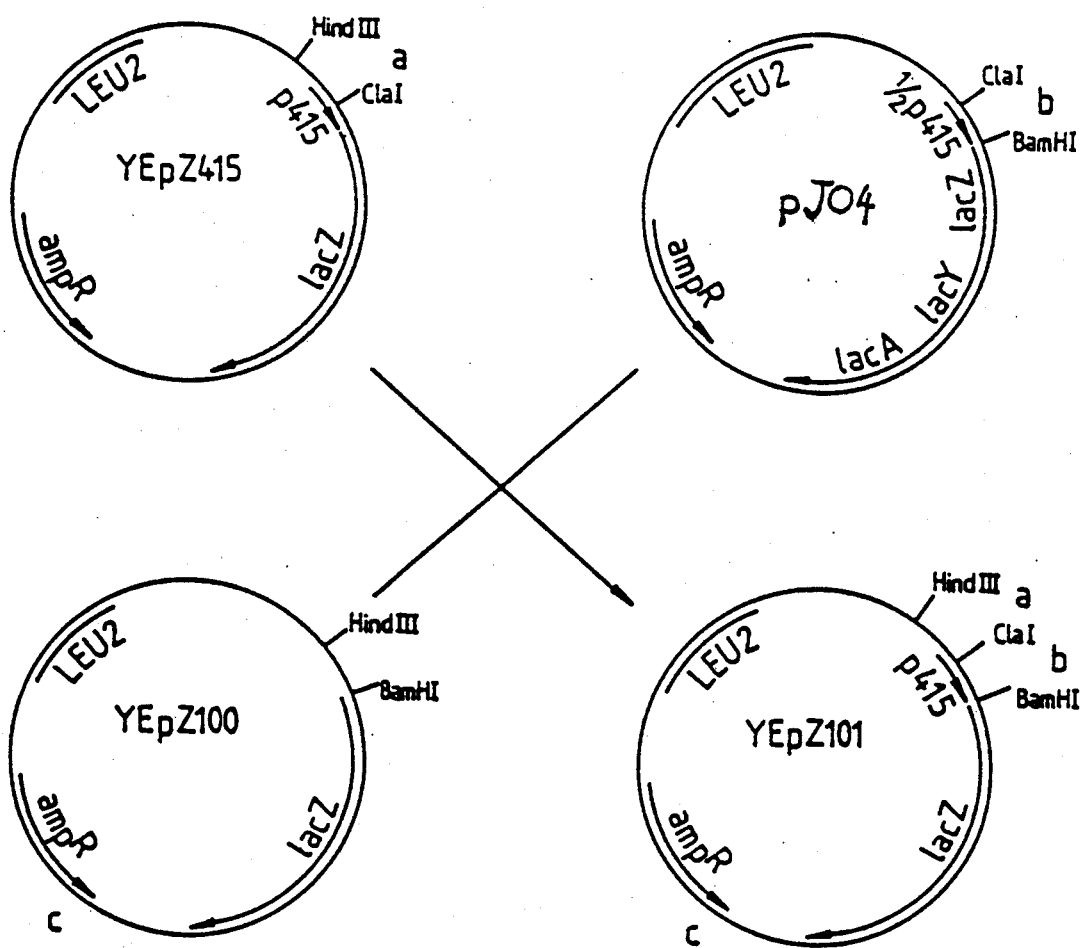

2.3 YEpZ101 was then constructed by combining DNA fragments from three of the plasmids described above, by a process involving three ligation events (FIG. 6). In this construction, the lacZ gene, the amp$^R$ gene, the replication origin in E. coli, the LEU2 gene, and the replication origin in S. cerevisiae (from the 2-micron plasmid) all derive from YEpZ100. The promoter p415 is reconstituted intact from two parts: (a) the 5' terminal half from the HindIII-ClaI fragment of YEpZ415, and (b) the 3' proximal half from the ClaI-BamHI fragment from pJ04. The next result of these operations is that the promoter p415 is now bounded by a unique HindIII site upstream and a unique BamHI site downstream, the latter being able to serve for the introduction of foreign genes as described below.

2.4 The plasmid YEpZ101 constructed as just described was used to transform the yeast. By operating as described in the preceding example, there was obtained a specific β-galactosidase activity identical to that conferred by plasmid YEpZ415.

3. Expression of the chicken lysozyme gene in S. cerevusuae by plasmids plysΔ 49 and plysΔ 59

To express in yeast the chicken lysozyme gene, plasmid plysΔ 9 was available which comprises the complete full cDNA of chicken lysozyme with its own ATG codon as described in Belgian patent No. 901,223. This cDNA had still to be appropriately combined with a yeast promoter as described for the β-galactosidase gene in the preceding example. However, for the reasons given above, as said cDNA comprises its own ATG initiation codon, it was not possible for this construction to use a plasmid such as YEpZ101 comprising promoter p415 which itself comprises an ATG codon. A variant of this plasmid free from this ATG codon was therefore required.

Figure 7:
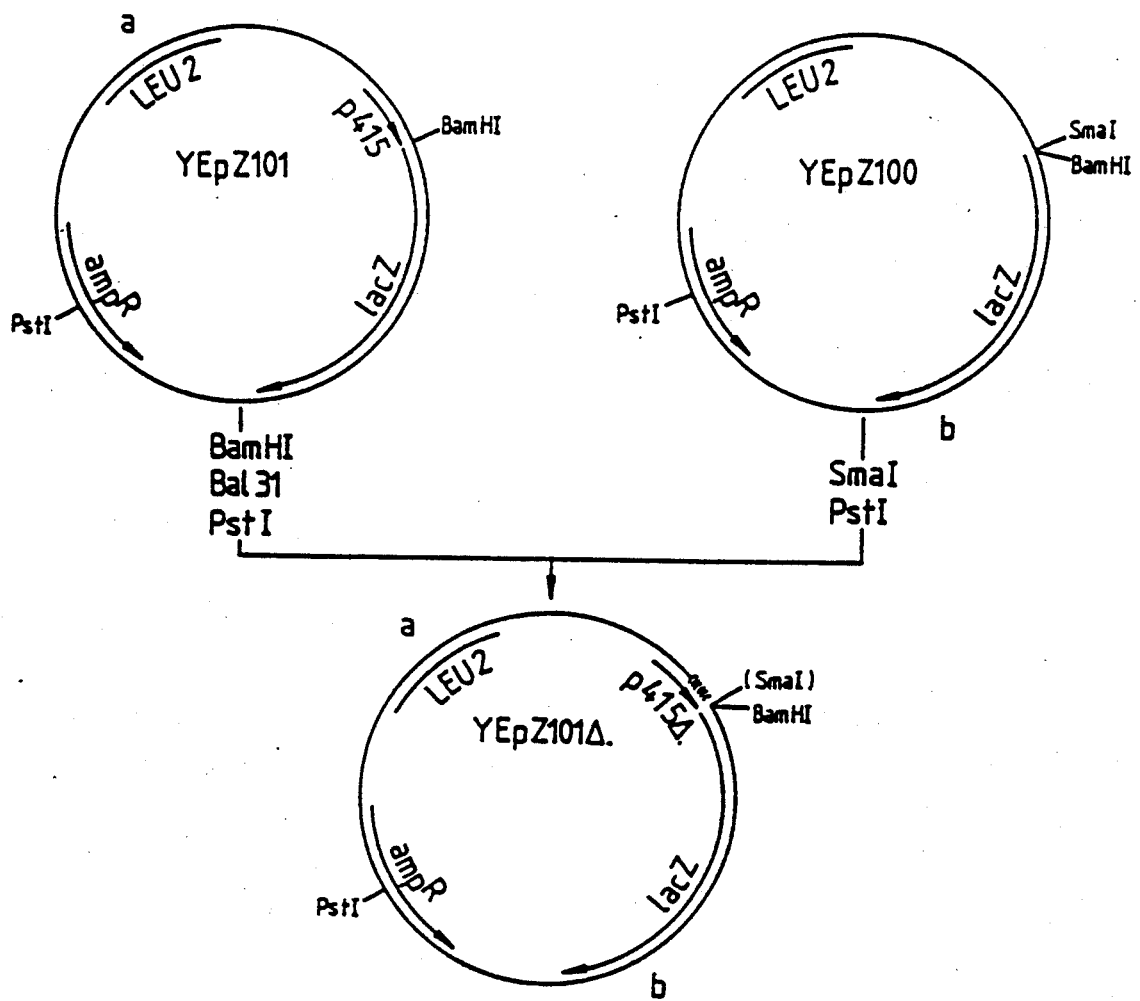
FIG. 7 represents the construction, from plasmids YEpZ100 and YEpZ101, of plasmids YEpZ101Δ comprising several variants of promoter p415 obtained by deletions carried out with Ba131 enzyme. The variants thus obtained (p415Δ 2, p415Δ 4 and p415Δ 5) are shown in FIG. 8.

3.1 A series of unidirectional deletions was made with enzyme Ba131 starting from site BamHI of YEpZ101. The plasmids thus shortened were then cleaved at the unique PstI site, and the fragments between the PstI site and the end digested by Ba131 were inserted between the PstI and SmaI sites of plasmid YEpZ100 (FIG. 7). This operation has two results:
(i) The ATG initiation codon immediately upstream of the BamHI site of YEpZ101 is destroyed;
(ii) the BamHI site is also destroyed but it is restored by fusion of the deleted end point with the SmaI site adjacent to the BamHI site in plasmid YEpZ100.

Figure 8:
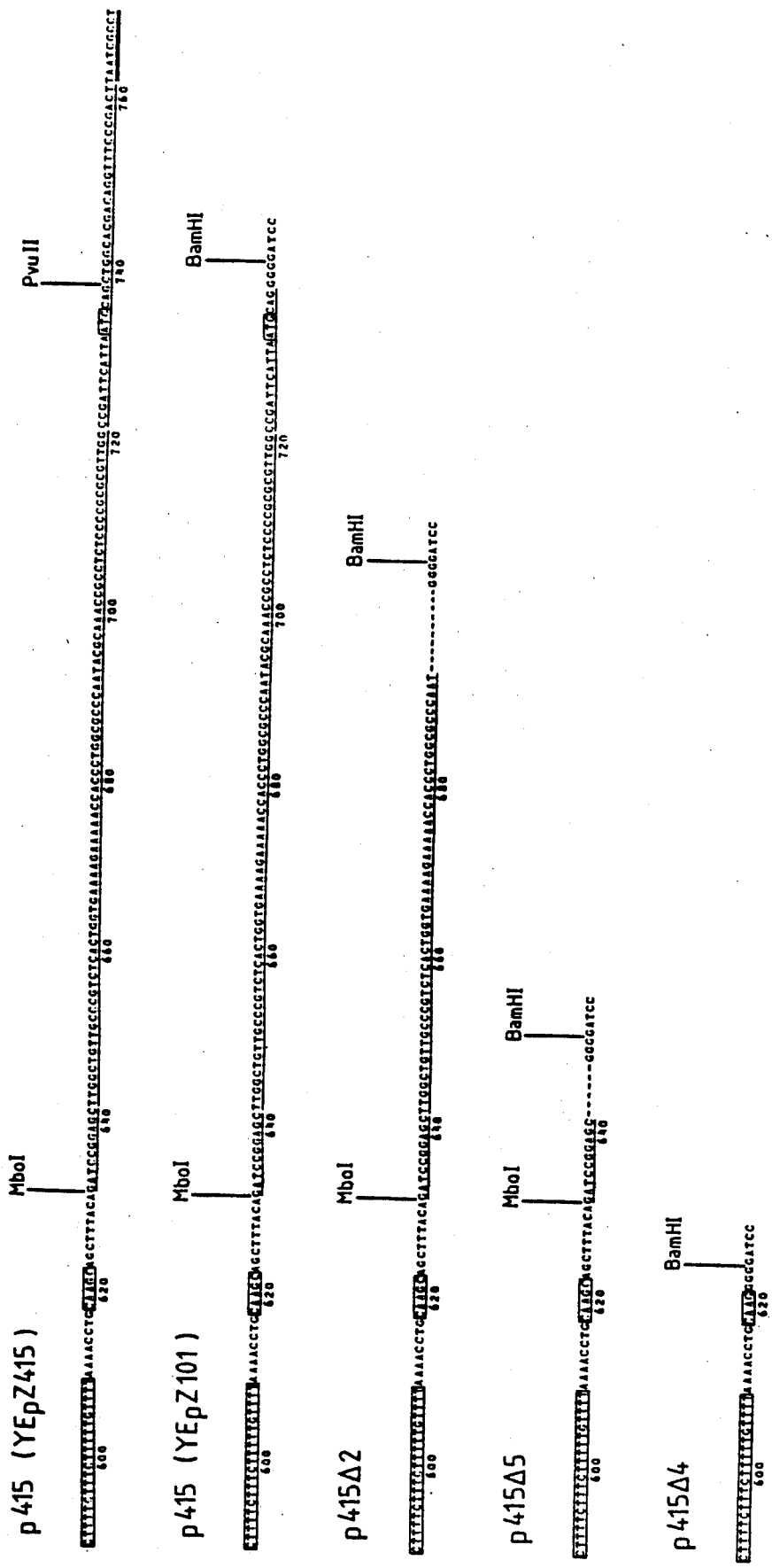

The deletions thus carried out resulted in promoters p415Δ 2, p415Δ 4 and p415Δ 5 (FIG. 8), carried by plasmids YEpZ101Δ 2, YEpZ101Δ 4 and YEpZ101Δ 5, respectively.

3.2 The promoters thus obtained had still to be associated, through an appropriate construction, with the chicken cDNA carried by plasmid plysΔ 9. In the case of promoter p415Δ Z, this construction was made by simultaneous ligation of the five following fragments:
(a) a HindIII-BamHI fragment from plasmid YEpZ101 2, comprising promoter p415Δ 2;
(b) a SphI-BamHI fragment from plysΔ 9, comprising the complete cDNA of lysozyme;
(c) an EcoRI-SphI fragment from plasmid pK01 (M. McKenney et al., in "Gene amplification and analysis", J. G. Chririkjan & T. Panas editors, Elsevier/North Holland, New York, 1981, p. 383) to be used as a junction between fragments (b) and (d);
(d) a PstI-EcoRI fragment from plasmid YEpZ415 comprising the origin of replication and one-half of the β-lactamase gene of pBR322; and
(e) a HindIII-PstI fragment from pJDB207 comprising the 2-micron-LEU2 segment and other half of the β-lactamase gene.

Figure 9:
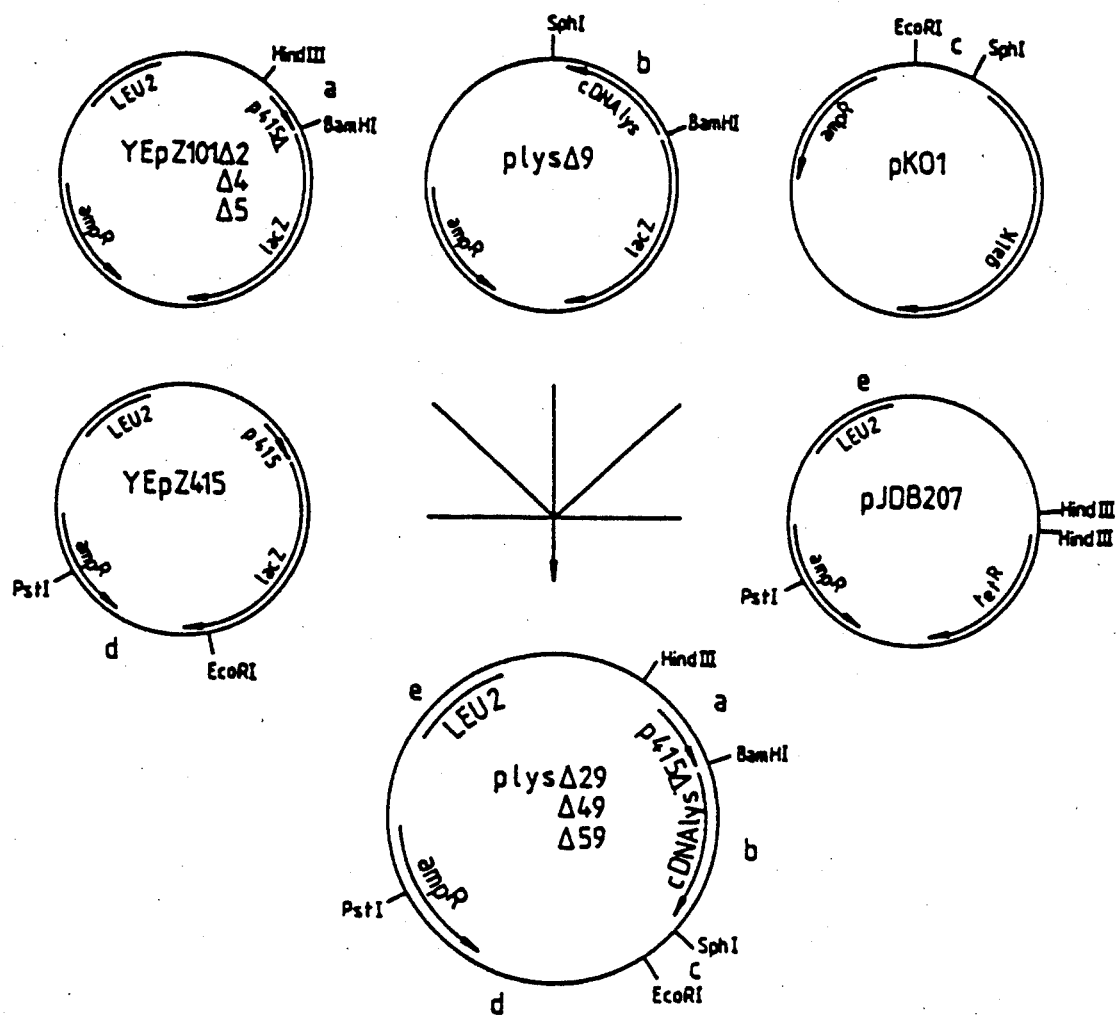
FIG. 9 represents the construction of vectors plys29, plys49 and plys59 carrying chicken lysozyme cDNA. This construction was made by univocal ligation of 5 purified fragments from plasmids YEpZ415, YEpZ101Δ, plysΔ 9, pK01 and pJDB207.

Before ligation, these various fragments were purified, and, since they have different and complementary sticky ends, only one viable plasmid resulted from this ligation: plysΔ 29 (FIG. 9).

By proceeding in the same way with two other fragments derived by deletion from promoter p415 (p415Δ 4 and p415Δ 5), two other plasmids were produced: plysΔ 49 and plysΔ 59. These three plasmids thus only differ by the fact that the promoter is positioned at various distances from the lysozyme cDNA, this resulting during transcription in different distances between the beginning (the 5' end) of the corresponding messenger RNAs and the natural AUG translation start site.

3.3 The plasmids constructed as described hereabove were then transformed into GRF18 strain (Leu−, His−) of the yeast S. cerevisiae, followed by selection for clones prototrophic for leucine (Leu+).

Figure 10:
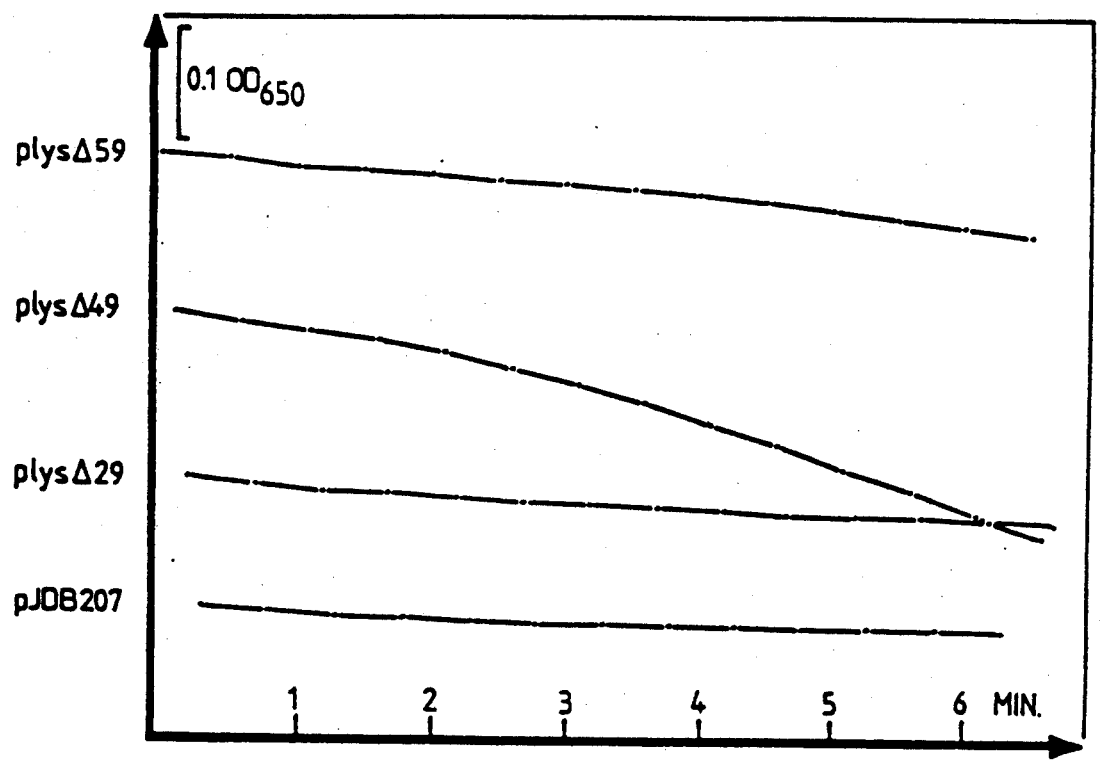
FIG. 10 shows that all extracts of yeast transformed by plasmids plysΔ 49 and plysΔ 59 are capable of lysing E. coli cells treated with EDTA to render them sensitive to lysozyme action.

These clones were then ground with glass beads, and the obtained lysates were clarified by centrifugation. Their lysozyme activity was tested by determining the decrease in optical density of a suspension of E. coli cells by the method of McMacken et al. (J. Mol. Biol. 49, 1970, 639). In FIG. 10, the initial values of the optical density at 650 nm ($OD_{650}$) were identical for all clones (0.7), but they have been shifted on the diagram for clarity. The results of FIG. 10 show a significant activity for GRF18 (plysΔ 49), and somewhat less for cells transformed by plasmid plysΔ 59.

Similar results were obtained by using a method in which the cells used as indicators for the action of lysozyme were those of the bacterium Micrococcus lysodeikticus (G. Alderton et al., J. Biol. Chem. 157, 1945, 43).

In a different type of assay, lysozyme was evidenced around transformed colonies growing on Petri dishes covered with a lawn of M. lysodeikticus. In this case, lysozyme expression was visualized by a transparent halo of bacterial lysis around the colonies. In agreement with the results using cell-free lysates, the halo of lysis was greatest with plysΔ 49 indicating that this clone was the best producer of lysozyme. This result also showed that the lysozyme is exported from the yeast cell since it must of necessity be extracellular in order to lyse the bacterial indicator.

FIG. 10 also shows that by operating in the same way with the plysΔ 29 clone, no cell lysis could be observed. The sequences responsible for the promoter function should therefore not only be present upstream of the gene to express, but also be suitably positioned with respect to this gene.

4. Expression of chicken lysozyme in S. cerevisiae by vector plys50

4.1 The vector pJDB207 upon which the lysozyme expression plasmids plysΔ 29, plysΔ 49 and plysΔ 59 (described hereinabove) are based, do not contain the entire 2-micron yeast plasmid and is consequently dependent on the presence of the endogenous 2-micron plasmid (found in most strains of S. cerevisiae) for its continued maintenance. This leads to such an unstable situation that the pJDB207-type plasmids are frequently lost from the cell (E. Erhaert and C. P. Hollenberg, J. Bacteriol. 156, 1983, 625, and M. Jarayam et al., Cell 34, 1983, 95). In contrast, the natural 2-micron plasmid is stably inherited. It is indeed known that plasmids constructed in such a way that they contain the entire 2-micron plasmid pJDB219, are more stable than those of the pJDB207-type (C. P. Hollenberg, Curr. Top. Microbiol. Immunol. 96, 1982, 119; R. M. Walmsley et al., Mol. Gen. Genet. 1983, 361). Such plasmids are therefore more useful for long-term growth, as for example in industrial fermentations.

Figure 11:
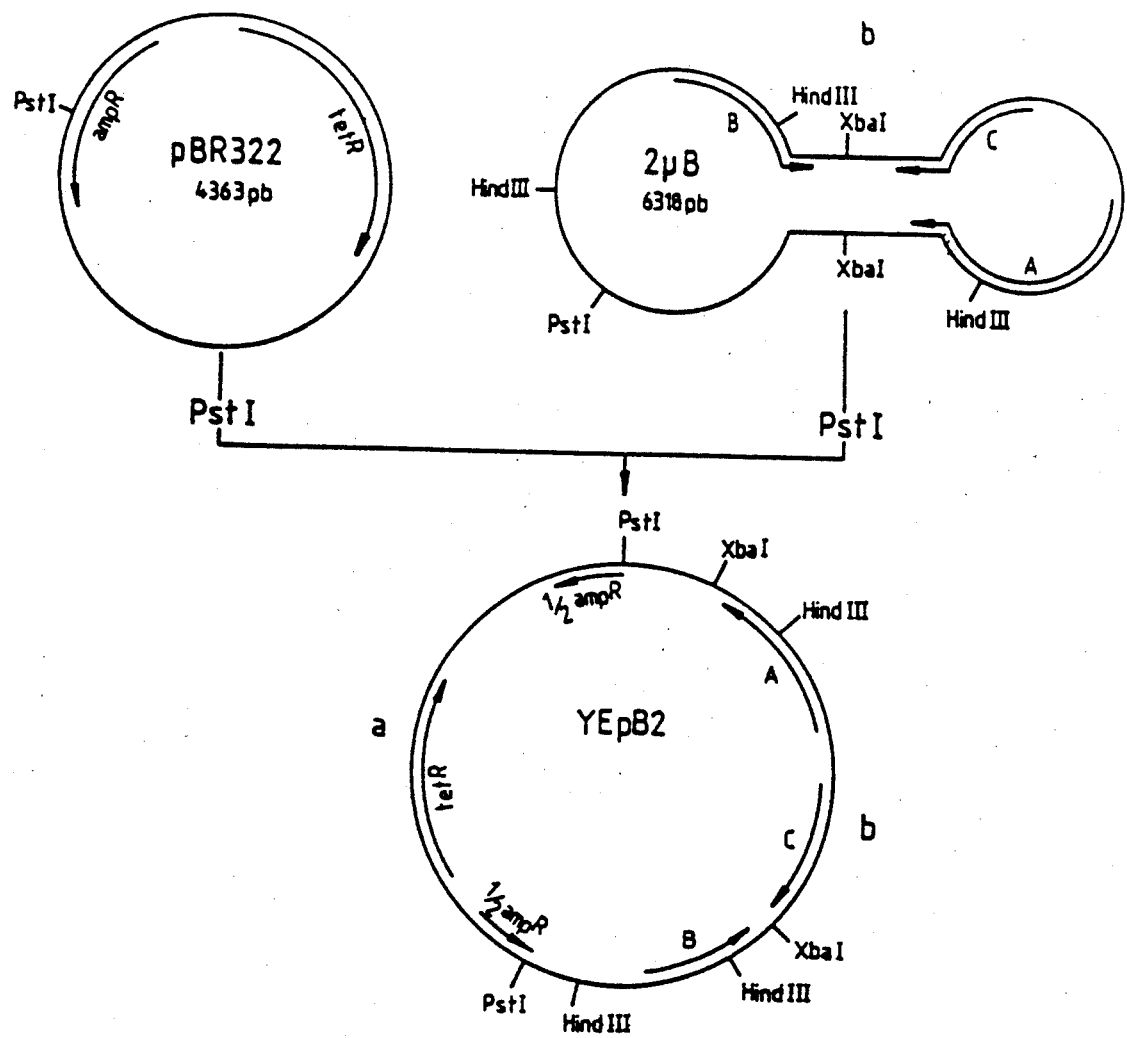
FIG. 11 represents the construction of plasmid YEpB2 by ligation of the fragments obtained by the action of PstI restriction enzyme on plasmid pBR322 and on the 2-micron yeast endogenous plasmid.
Figure 12:
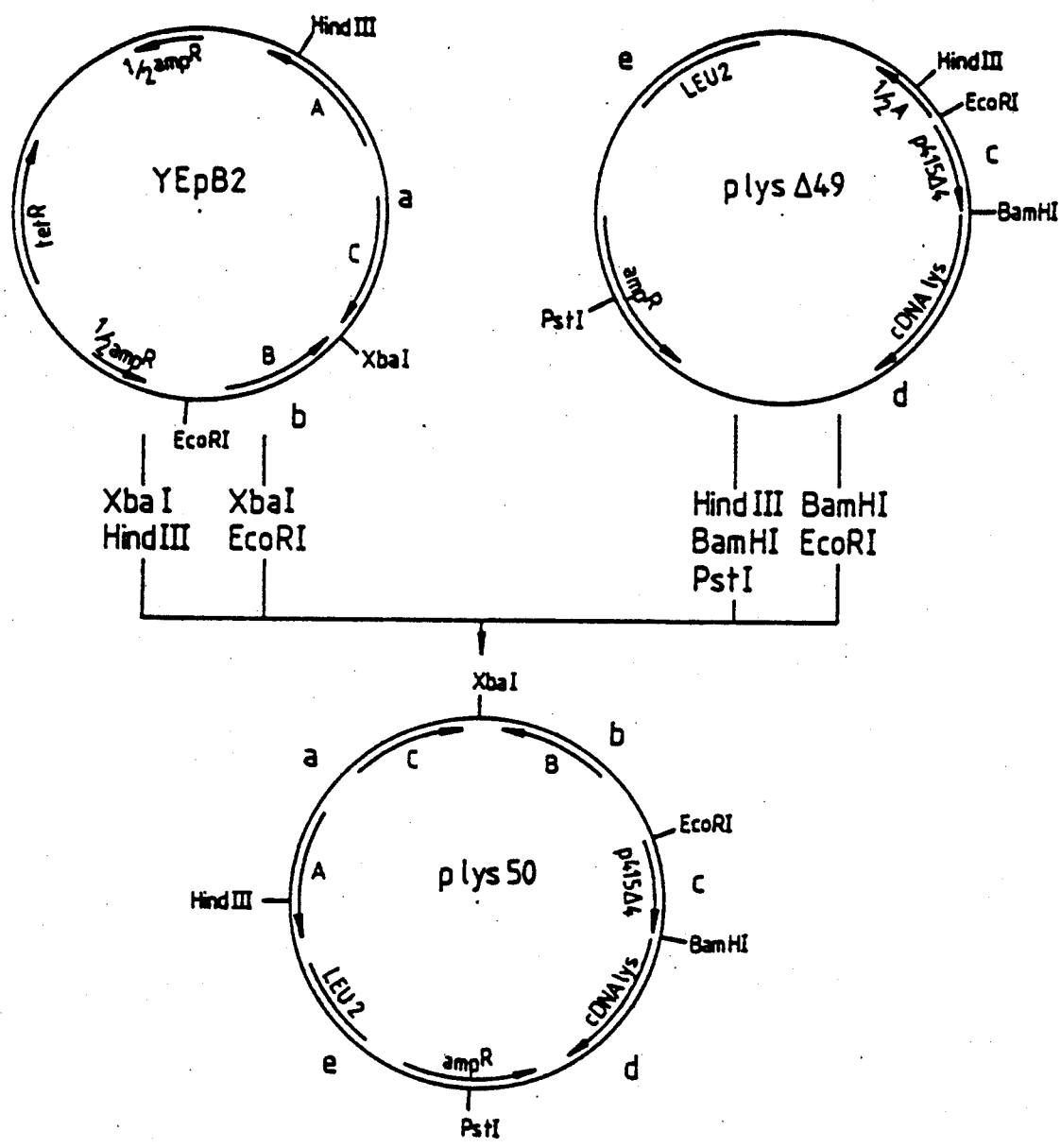
FIG. 12 represents the construction of the expression vector plys50 by univocal ligation of five purified fragments from plasmids YEpB2 and plysΔ 49.

To construct such a complete 2-micron vector, plasmid YEpB2 (FIG. 11) was used, which was previously made by cloning the entire 2-micron plasmid into pBR322 at their mutually unique PstI sites. Two fragments from YEpB2 and two fragments from plysΔ 49 were then combined to give plys50 (FIG. 12). In this plasmid, the three 2-micron genes A, B and C are intact and the lysozyme gene is expressed from the p415Δ 4 promoter as in plysΔ 49 described in the preceding example.

4.2 After transforming the GRF18 strain (His−, Leu−) of *S. cerevisiae* by plasmids plys50 and pJDB207, the transformed cells obtained in both cases were separately grown on a minimum medium supplemented with histidine (0.002%). When the cultures had reached the stationary phase (optical density of about 5) (cell dry weight=about 1.5 g/l of culture), the cells were separated from the culture medium by centrifugation, suspended in a 0.1M pH 7 phosphate buffer, and grinded with glass beads. Lysozyme activity in the supernatant and the lysate from both cultures was determined by their ability to lyse *M. lysodeikticus* cells according to the method of D. Shugar (Biochem. Biophys. Acta, 8, 1952, 302). No activity was detected in a homogenate of the strain transformed by plasmid pJDB207, whereas a lysozyme activity of 35 units per ml of culture could be shown for that of strain GRF18 (plys50).

By determining total proteins according to the method of D. Herbert et al. (Methods in MIcrobiol. 5B, 1971, 209) as modified by C. Wang and R. L. Smith (Anal. Biochem. 63, 1975, 414), taking into account the specific activity of commercial purified lysozyme (Boehringer Mannheim), it was found that lysozyme produced by yeast in the above conditions accounts for about 0.8% of the soluble yeast proteins.

Strains GRF18 (plysΔ 49) and AH22cir° (plys50) were deposited on Dec. 5, 1984 at the Centraal Bureau voor Schimmelcultures, Oosterstraat 1, P.O. Box 273, NL—3740 AG Baarn (The Netherlands) where they have been respectively given accession numbers CBS 7130 and CBS 7129.

A sample of *E. Coli* MC 1065, carrying plasmid YpeZ415 containing promoter SEQUENCE I was deposited on May 26, 1988 at the Centraal Bureau voor Schimmelcultures, Oosterstraat 1, Box 273 NL 3740 AG Baarn, The Netherlands, where it has been given accession number CBS 414.88.

What is claimed is:

1. A promoter capable of ensuring expression in yeast of genes coding for heterologous polypeptides, said promoter comprising: a DNA fragment, or mutants or sub-fragments thereof wherein said mutants or subfragments retain the promoter function, said promoter comprising a nucleotide sequence beginning with an EcoRI site and selected from the group of sequences consisting of SEQUENCE ONE (as shown in FIG. 3, nucleotides No. 1-735), SEQUENCE TWO (as shown in FIG. 13), and SEQUENCE THREE (as shown in FIG. 14), and comprising another restriction site which immediately follows said sequences.

2. The promoter according to claim 1, wherein said other restriction site is selected from the group of sites consisting of PvuII, BamHI, EcoRI, ClaI, HindIII, SphI, SalI, SacI, PstI, XbaI and XhoI.

3. The promoter according to claim 1, having the nucleotide sequence:

```
         10        20        30        40        50        60        70
GAATTCACTGGATTCCTTCCTTCCGGTACCAATATCACTGTAAATATGTCTTCAGATCCTTGAACTGGAA 80        90       100       110       120       130       140
GTATTTAGGGTCCCTGACTTTCATCAACTGAAAGTCAAGCTCATTTGTAAATTGTCCCCTCTTTTTATAC 150       160       170       180       190       200       210
AAATTTTCTGGCAGAATTGACAGGAAATCCTCCTTAACTAAATATGGATTGTAGCTTCTATATTGTAAGA 220       230       240       250       260       270       280
CAGAAGGTTTCTTTTCCTGCAACTGCTGCTGCTTATTAACAGATGCCGTTTTCTCACTTATTGTTGCTGA 290       300       310       320       330       340       350
ATTTCCTGACTCTACGGAGCCAAGAACTCTTCCCGTGGACTTCAGATGGTTCAGTACTAATTTAATAGCT 360       370       380       390       400       410       420
TTACTAGAAGCCTTCATATCTGCTTTACATCGATGACAAAGGGATAATGGGTAGAGTCTGGCACTCCTAC 430       440       450       460       470       480       490
CCTAAATTGTTAACTTCCTATTTGAGTTCGTGGTGTTAGTATTCTCATCACGATTAACGAATATGAAAAA 500       510       520       530       540       550       560
AAAAATTGAAAATTTTGTAGAAACGGAGTGCTCAGTATAAAAAGCGCATAGTAAGACTTTTTGTTAAATG 570       580       590       600       610       620       630
TTTCTTTCCTCCTATACATTTTCACATACTTTTCTTTCTTTTTGTTTTAAAACCTGCAAGCAGCTTTACA 640       650       660       670       680       690       700
GATCCGGAGCTTGGCTGTTGCCCGTCTCACTGGTGAAAAGAAAAACCACCCTGGCGCCCAATACGCAAAC 710       720       730       740
CGCCTCTCCCCGCGCGTTGGCCGATTCATTAATGCAGCTG.
```

4. The promoter according to claim 1, having the nucleotide sequence:

```
         10        20        30        40        50        60        70
GAATTCACTGGATTCCTTCCTACCGGTACCAATATCACTGTAAATATGTCTTCAGATCCTTGAACTGGAA 80        90       100       110       120       130       140
GTATTTAGGGTCCCTGACTTTCATCAACTGAAAGTCAAGCTCATTTGTAAATTGTCCCCTCTTTTTATAC 150       160       170       180       190       200       210
AAATTTTCTGGCAGAATTGACAGGAAATCCTCCTTAACTAAATATGGATTGTAGCTTCTATATTGTAAGA
```

```
                220         230        240          250        260         270        280
CAGAAGGTTTCTTTTCCTGCAACTGCTGCTGCTTATTAACAGATGCCGTTTTCTCACTTATTGTTGCTGA 290         300        310         320         330        340         350
ATTTCCTGACTCTACGGAGCCAAGAACTCTTCCCGTGGACTTCAGATGGTTCAGTACTAATTTAATAGCT 360         370        380         390        400         410         420
TTACTAGAAGCCTTCATATCTGCTTTACATCGATGACAAAGGGATAATGGGTAGAGTCTGGCACTCCTAC 430         440        450         460        470         480         490
CCTAAATTGTTAACTTCCTATTTGAGTTCGTGGTGTTAGTATTCTCATCACGATTAACGAATATGAAAAA 500         510        520         530        540         550         560
AAAAATTGAAAATTTTGTAGAAACGGAGTGCTCAGTATAAAAAGCGCATAGTAAGACTTTTTGTTAAATG 570         580        590         600        610         620         630
TTTCTTTCCTCCTATACATTTTCACATACTTTTCTTTCTTTTTGTTTTAAAACCTGCAAGCAGCTTTACA 640         650        660         670        680         690        700
GATCCGGAGCTTGGCTGTTGCCCGTCTCACTGGTGAAAAGAAAAACCACCCTGGCGCCCAATACGCAAAC 710         720        730         740
CGCCTCTCCCCGCGCGTTGGCCGATTCATTAATGCAGGGGGATCC.
```

5. The promoter according to claim 1, having the nucleotide sequence:

```
         10          20         30          40         50          60         70
GAATTCACTGGATTCCTTCCTACCGGTACCAATATCACTGTAAATATGTCTTCAGATCCTTGAACTGGAA 80          90        100         110        120         130        140
GTATTTAGGGTCCCTGACTTTCATCAACTGAAAGTCAAGCTCATTTGTAAATTGTCCCCTCTTTTTATAC 150         160        170         180        190         200        210
AAATTTTCTGGCAGAATTGACAGGAAATCCTCCTTAACTAAATATGGATTGTAGCTTCTATATTGTAAGA 220         230        240          250        260         270        280
CAGAAGGTTTCTTTTCCTGCAACTGCTGCTGCTTATTAACAGATGCCGTTTTCTCACTTATTGTTGCTGA 290         300        310         320         330        340         350
ATTTCCTGACTCTACGGAGCCAAGAACTCTTCCCGTGGACTTCAGATGGTTCAGTACTAATTTAATAGCT 360         370        380         390        400         410         420
TTACTAGAAGCCTTCATATCTGCTTTACATCGATGACAAAGGGATAATGGGTAGAGTCTGGCACTCCTAC 430         440        450         460        470         480         490
CCTAAATTGTTAACTTCCTATTTGAGTTCGTGGTGTTAGTATTCTCATCACGATTAACGAATATGAAAAA 500         510        520         530        540         550         560
AAAAATTGAAAATTTTGTAGAAACGGAGTGCTCAGTATAAAAAGCGCATAGTAAGACTTTTTGTTAAATG 570         580        590         600        610         620         630
TTTCTTTCCTCCTATACATTTTCACATACTTTTCTTTCTTTTTGTTTTAAAACCTGCAAGGGGGGATCC.
```

8. The vector plasmid according to claim 6, comprising at least one replication ensuring sequence from the 2-micron plasmid, said sequence including at least the replication origin of the 2-micron plasmid.

9. The vector plasmid according to claim 6, said vector plasmid further comprising a marker gene which enables exertion of a positive selection pressure on yeast transformed by this plasmid.

10. The vector plasmid according to claim 6, wherein said plasmid is plysΔ 49.

11. The vector plasmid according to claim 6, wherein said plasmid is plysΔ 59.

12. The vector plasmid according to claim 6, wherein said plasmid is plys50.

13. A transformed yeast, said transformed yeast comprising a vector plasmid containing a promoter and being capable of autonomous replication in said yeast and being capable of ensuring expression of a DNA fragment coding for heterologous polypeptides;

said promoter being capable of ensuring expression in yeast of genes coding for heterologous polypeptides, said promoter comprising: a DNA fragment, or mutants or sub-fragments thereof wherein said 6. A vector plasmid capable of autonomous replication in yeast and being capable of ensuring expression of a DNA fragment coding for heterologous polypeptides; said vector plasmid containing a promoter capable of ensuring expression in yeast of genes coding for heterologous polypeptides, said promoter comprising: a DNA fragment, or mutants or sub-fragments thereof wherein said mutants or sub-fragments retain the promoter function, said promoter comprising a nucleotide sequence beginning with an EcoRI site and selected from the group of sequences consisting of SEQUENCE ONE (as shown in FIG. 3, nucleotides No. 1-735), SEQUENCE TWO (as shown in FIG. 13), and SEQUENCE THREE (as shown in FIG. 14), and comprising another restriction site which immediately follows said sequences.

7. The vector plasmid according to claim 6, wherein said other restriction site is selected from the group of sites consisting of PvuII, BamHI, EcoRI, ClaI, HindIII, SphI, SalI, SacI, PstI, XbaI and XhoI.

mutants or sub-fragments retain the promoter function, said promoter comprising a nucleotide sequence beginning with an EcoRI site and selected from the group of sequences consisting of SEQUENCE ONE (as shown in FIG. 3), nucleotides No. 1-735), SEQUENCE TWO (as shown in FIG. 13), and SEQUENCE THREE (as shown in FIG. 14) and comprising another restriction site which immediately follows said sequences.

14. The transformed yeast according to claim 13, wherein said other restriction site is selected from the group of sites consisting of PvuII, BamHI, EcoRI, ClaI, HindIII, SphI, SalI, SacI, PstI, XbaI and XhoI.

15. The transformed yeast according to claim 13, wherein said yeast belongs to the *Saccharomyces* genus.

16. The transformed yeast according to claim 15, wherein said yeast belongs to the *Saccharomyces cerevisiae* species.

17. The transformed yeast according to claim 16, wherein said yeast is selected from the group consisting of strains AH22 and GRF18.

18. A process for preparing polypeptides, said process comprising culturing a transformed yeast and recovering a heterologous polypeptide produced by said culturing, said transformed yeast comprising a vector plasmid containing a promoter and being capable of autonomous replication in said yeast and being capable of ensuring expression of a DNA fragment coding for heterologous polypeptides;

said promoter being capable of ensuring expression in yeast of genes coding for heterologous polypeptides, said promoter comprising: a DNA fragment, or mutants or sub-fragments thereof wherein said mutants or sub-fragments retain the promoter function, said promoter comprising a nucleotide sequence beginning with an EcoRI site and selected from the group of sequences consisting of SEQUENCE ONE (as shown in FIG. 3, nucleotides No. 1-735), SEQUENCE TWO (as shown in FIG. 13), and SEQUENCE THREE (as shown in FIG. 14), and comprising another restriction site which immediately follows said sequences.

19. The process according to claim 18, wherein said other restriction site is selected from the group of sites consisting of PvuII, BamHI, EcoRI, ClaI, HindIII, SphI, SalI, SacI, PstI, XbaI and XhoI.

20. The process according to claim 18, wherein said polypeptide comprises a 1,4-$\beta$-N-acetylmuramidase.

* * * * *